United States Patent
Møller et al.

(10) Patent No.: US 8,062,650 B2
(45) Date of Patent: Nov. 22, 2011

(54) BIOLOGICALLY INHIBITING MATERIAL A METHOD OF PRODUCING SAID MATERIAL AS WELL AS THE USE OF SAID MATERIAL FOR INHIBITING LIVE CELLS

(75) Inventors: Per Møller, Esrum (DK); Erik-Ole Jensen, Hasselager (DK); Lisbeth Rischel Hilbert, Holte (DK)

(73) Assignee: Alfa Laval Corporate AB, Lund (SE)

( * ) Notice: Subject to any disclaimer, the term of this patent is extended or adjusted under 35 U.S.C. 154(b) by 104 days.

(21) Appl. No.: 10/536,248

(22) PCT Filed: Nov. 19, 2003

(86) PCT No.: PCT/DK03/00790
§ 371 (c)(1),
(2), (4) Date: May 19, 2005

(87) PCT Pub. No.: WO2004/045577
PCT Pub. Date: Jun. 3, 2004

(65) Prior Publication Data
US 2006/0003019 A1    Jan. 5, 2006

(30) Foreign Application Priority Data
Nov. 19, 2002   (DK) ................................ 2002 01782

(51) Int. Cl.
*A01N 25/00* (2006.01)
*A61K 33/24* (2006.01)
*A61K 33/38* (2006.01)
*A61K 31/28* (2006.01)
*A01N 59/16* (2006.01)
*A01N 55/02* (2006.01)

(52) U.S. Cl. ........ 424/405; 424/617; 424/618; 514/492; 514/495

(58) Field of Classification Search ........................ None
See application file for complete search history.

(56) References Cited

U.S. PATENT DOCUMENTS

| | | | |
|---|---|---|---|
| 4,886,505 A | 12/1989 | Haynes et al. | 604/265 |
| 5,295,979 A | 3/1994 | DeLaurentis et al. | 604/265 |
| 5,322,520 A * | 6/1994 | Milder | 604/265 |
| 5,520,664 A * | 5/1996 | Bricault et al. | 604/265 |
| 5,843,186 A | 12/1998 | Christ | 623/6 |
| 6,287,484 B1 | 9/2001 | Hausslein et al. | 252/512 |

FOREIGN PATENT DOCUMENTS

| | | |
|---|---|---|
| JP | 7048202 A | 2/1995 |
| JP | 9071897 A | 3/1997 |
| JP | 2000060513 A | 2/2000 |
| WO | WO 95/18637 | 7/1995 |

OTHER PUBLICATIONS

Dowling et al. Surface and Coatings Technology 2003, 163-164, 637-640.*

* cited by examiner

*Primary Examiner* — Ernst Arnold
(74) *Attorney, Agent, or Firm* — The Nath Law Group; Joshua B. Goldberg; Tanya E. Harkins

(57) ABSTRACT

Method for inhibiting live cells including eukaryotic and prokaryotic cells on an item utilized outside the human or animal body. The method includes the step of providing on the item a biologically inhibiting material including an anode material and a cathode material. Both the anode material and the cathode material have a positive galvanic potential, and the potential of the cathode material is higher than the potential of the anode material. The anode material and the cathode material each include exposed active surfaces. The exposed active surfaces include at least one of a plurality of separated areas of anode material and a plurality of separated areas of cathode material. A distance between any point on the active surface and both the adjacent cathode material and the adjacent anode material does not exceed 200 μm for inhibiting live cells including eukaryotic and prokaryotic cells on the item utilized outside the human or animal body.

19 Claims, 1 Drawing Sheet

BIOLOGICALLY INHIBITING MATERIAL A METHOD OF PRODUCING SAID MATERIAL AS WELL AS THE USE OF SAID MATERIAL FOR INHIBITING LIVE CELLS

This application is a 371 of PCT/DK03/00790 filed on Nov. 19, 2003 and claims priority to foreign application Denmark PA 2002-01782 filed on Nov. 19, 2002.

TECHNICAL FIELD

The present invention relates to a biologically inhibiting material including an anode material and a cathode material, where the anode material and the cathode material both have a positive galvanic potential, and where the potential of the cathode material is more positive than the potential of the anode material. Due to this difference in the potentials, the biologically inhibiting material will act as a galvanic element in contact with an electrolyte. The invention also relates to a method of producing the material as well as to the use of the material for inhibiting live cells.

TECHNICAL BACKGROUND

Good hygiene is an essential factor in the food production field. Many resources are invested in cleaning and disinfecting the equipment to improve the shelf-life of the products. In addition, during recent years the attention has been focussed on the risk of contamination of food products with pathogenic bacteria. Accordingly, there is an increasing demand for improvements in the field of good hygiene not only with respect to the cleaning, but also in relation to the suitable design of the machines used for the production.

Since 1 Jan. 1995 the EU has prescribed that the machines for processing food products must be designed to support good hygiene and an efficient cleaning procedure which ensures an optimum food product safety. Accordingly, an obvious demand exists for systematically optimizing the hygienic design of machines for processing food products.

An optimum cleaning of a closed process equipment is obtained by ensuring that the cleaning fluids circulate at a sufficiently high flow rate providing turbulent flow throughout the entire process equipment. Dead areas involving a very low flow rate should therefore be avoided by suitable equipment design.

Despite the above efforts, it can be difficult to completely avoid areas in the process equipment in which small remnants of food products stick to the walls of the equipment or accumulate in small pockets and thereby provide growth conditions for unwanted and often pathogenic micro-organisms. As these micro-organisms grow very quickly in the food products being processed in the process equipment, such small residues can very quickly have a serious effect on both health and costs.

Presently, attempts are made to develop materials on which there will be a reduced tendency to form biofilm. Examples are materials having a reduced adhesion to protein and fat and micro-organisms. However, such a solution is unlikely to prevent food remnants and micro-organisms from accumulating in small pockets and cracks. Accordingly, a demand exists for a material with inherent antimicrobial properties.

U.S. Pat. No. 5,843,186 (Christ) discloses an intraocular plastic lens (IOL) with antibacterial activity based on an iontophoretic effect. At least a portion of the lens is made of an iontophoretic composite material including two components, such as silver and platinum, with different galvanic potentials dispersed in a conducting polymer matrix. The iontophoretic effect is obtained when the lens is implanted in an eye. Here saline body fluids penetrate into the polymer matrix and establish a galvanic element between the two embedded components, which causes the ions of one component to dissolve whereafter the ions can migrate out of the matrix and into the surrounding body fluid, where they exert an antibacterial effect. In order to protect the body against harm, the galvanic elements are per se isolated from direct body contact in the surrounding polymer matrix, strong electric field strengths optionally being generated adjacent said galvanic elements.

Due to the use of this known ocular implantate in contact with the eye the antibacterial effect thereof is adjusted to ensure that the body does not suffer any acute or accumulated harm. It is also important that an accumulation of antibacterial ions is avoided for a short or long period.

However, an antibacterial effect based on the iontophoretic principle as suggested by U.S. Pat. No. 5,843,186 (Christ) and adjusted to be used in an implantate is unlikely to suffice for such antimicrobial or other cytocidal uses where the desired effect must be significantly stronger than hitherto known. In addition, an intensification of the effect to release an increased amount of antimicrobial ions results in an increased amount of ion residues in the solution or in the killed microorganism cells, which cannot be tolerated in many situations, such as in connection with processing of food products.

U.S. Pat. No. 4,886,505 (Haynes et al.) discloses an apparatus to be inserted in the body, such as a catheter. On the surfaces, this apparatus is coated with a first and a second metal in such a manner that a galvanic effect is provided when the apparatus is brought into contact with an electrolyte, such as a body fluid. It is suggested that the two metals are applied onto the surface of the catheter in form of very thin films of a thickness of approximately 5 to 500 nm, either one metal atop the other metal or in such a manner that portions are covered with one type of metal film while other portions are covered with the second type of metal film, a switch being coupled between said two types with the result that the galvanic effect can be switched on and off according to desire.

In one embodiment, the catheter is coated with two metal films, one over the other, and produces a galvanic effect resulting in relatively significant potential differences per distance, viz. high electric field strengths, in an area inaccessible to micro-organisms, i.e. the area at the contact surface between the two films. Thus the antimicrobial effect is based on metal ions being released in the contact layer despite the fact that they are attracted by the cathode material.

In another embodiment, approximately half the surface of the catheter is covered by one type of metal film while the remaining portion of said surface is covered by the second type of metal film apart from an intermediate non-covered portion where a switch is positioned. Here the galvanic effect is indeed active when in direct contact with the surrounding body fluids, but the relatively significant potential differences per distance, viz. the high electric field strengths, only apply to the interface area between the two metal films, whereas the potential difference per distance and consequently the electric field strength is significantly weaker in portions presenting a large distance to said interface area. According to the publication, the antimicrobial effect is obviously also based on released metal ions.

Accordingly, the principle suggested in U.S. Pat. No. 4,886,505 (Haynes et al.) cannot be used in situations where a strong galvanic effect with high electric field strengths across the entire surface is needed without involving a significant release of metal ions.

Therefore, a demand still exists for materials capable of efficiently inhibiting live cells across the entire surface of the material in such a manner that there are no areas or domains with an insufficient antimicrobial effect where unwanted micro-organisms can survive. Such materials are inter alia needed within the food industry where remaining live micro-organisms in the production equipment, during storage and during transport can cause serious problems such as rapid tainting of the product and disease-causing effects in the consumer. These problems are particularly serious when the processed food products are nutrient mediums for the micro-organisms in question and consequently can promote the growth of said micro-organisms. Such food products are for instance dairy products, meat and fish products, gravy, juice, lemonade, beer, wine or soft drinks.

BRIEF DESCRIPTION OF THE INVENTION

It turned out surprisingly that it is possible to obtain a particularly strong cell-inhibiting effect on a material which includes an anode material and a cathode material, said anode material and said cathode material forming a galvanic element in contact with an electrolyte, provided one or more surfaces of the material are designed so that any location on the surface is spaced a short distance from both the adjacent anode material and the adjacent cathode material.

Thus the invention relates to a biologically inhibiting material including an anode material and a cathode material, where both the anode material and the cathode material have a positive galvanic potential and where the potential of the cathode material is more positive than the potential of the anode material, said material being characterised in that it includes a surface with separated (discrete) areas of anode material and cathode material, where the distance between any point on the active surface and both the adjacent cathode material and the adjacent anode material does not exceed 200 µm.

The invention relates furthermore to a method of producing the biologically inhibiting material according to the invention, said method being characterised in that an incomplete layer of the second electrode material is applied onto a surface of the first electrode material by way of a conventional coating procedure in such a manner that the second electrode material is caused to partially cover the first electrode material or is integrated in a matrix of the first electrode material.

In addition, the invention relates to the use of the biologically inhibiting material for inhibiting or killing live cells.

The particular design of the surface of the material ensures that any point on the surface is positioned at a very short distance from the adjacent cathode and anode. As a result relatively strong potential differences are obtained per distance, viz. high electric field strengths. This is a clear improvement compared to the above embodiment described in U.S. Pat. No. 4,886,505 (Haynes et al.). In said embodiment the metal surfaces are divided into two halves. This means that it is only possible to obtain such high field strengths adjacent to the interface area in the immediate vicinity of both of the two different materials, whereas the electric field strength is significantly lower as the distance to the interface is increased. Correspondingly, the strong electric field strengths in the intraocular lens according to U.S. Pat. No. 5,843,186 (Christ) are generated inside the polymer matrix at a distance from the micro-organisms to be controlled.

An additional advantage of the biologically inhibiting material according to the invention is that the anode material—which can be made of silver—does not dissolve during the galvanic process and accordingly it does not release significant amounts of $Ag^+$-ions to the electrolyte. In fact the concentration of $Ag^+$-ions is very low and based on an equilibrium and no forced dissolution takes place. In this manner the inhibiting material can be used in the processing of products or materials where the presence of silver ions is undesirable.

The extent of the applicability of the invention appears from the following detailed description. It should, however, be understood that the detailed description and the specific examples are merely included to illustrate the preferred embodiments and that various alterations and modifications within the scope of protection will be obvious to persons skilled in the art on the basis of the detailed description.

DETAILED DESCRIPTION OF THE INVENTION

As mentioned above, the inhibiting material according to the invention has a surface with separated areas of the two electrode materials.

These areas are distributed on the active surface in such a manner that the distances between any point on the surface and the adjacent cathode material and between said point and the adjacent anode material do not exceed 200 µm. These distances are preferably shorter than 100 µm and typically considerably shorter.

A material meeting these requirements can be prepared starting with a material having a surface of one of the electrode materials followed by an incomplete coating procedure with the other electrode material. In this way an incomplete coverage with the second material is obtained.

A multitude of coating methods are available to the person skilled in the art for applying thin metal coatings onto a surface. This is also called a plating. It is well-known to the person skilled in the art to produce a metal coating by way of an appropriate choice of process parameters, such as processing time, concentration, temperature etc, where said metal coating completely covers the substrate surface in question in a desired layer thickness and without "skips" or "holes", i.e. areas with none or only a partial covering of the coating.

Instead of following the above knowledge of the person skilled in the art, the process parameters can be chosen so that a coating having an incomplete coverage is obtained. Thus the coating process can be carried out with a reduced processing time, a lowered temperature, a reduced concentration of active substances, a reduced current density of the electrolytic processes etc. with the result that an incomplete coating with skips is obtained where the underlying material is uncovered or where the coating appears in form of separated (discrete) clusters distributed on the underlying material.

Thus, the active surface of the biologically inhibiting material can be composed of separated areas in form of clusters of a cathode material distributed across a continuous area of an anode material, or separated areas in form of skips where the cathode material is uncovered and distributed in a continuous area of an anode material.

It is also possible that the active surface of the biologically inhibiting material can be composed of separated areas in form of clusters of an anode material distributed across a continuous area of a cathode material, or separated areas in form of skips where the anode material is uncovered and distributed in a continuous area of a cathode material.

Theoretically speaking, the two electrode materials can be distributed in any pattern across the surface merely provided that the necessary short distance to both electrode materials applies from any point on the surface to ensure a sufficiently high electric field strength and consequently a sufficiently strong biological inhibition anywhere on or in the immediate vicinity of the surface.

The anode material and the cathode material both have positive galvanic potentials (relative to SHE), and the potential of the cathode material is more positive than the potential of the anode material. As a result, a galvanic element is formed by the contact of the inhibiting material with an electrolyte.

The galvanic potential of one of these materials M means the standard potential $\epsilon_M$ of the reaction $$M^{n+}ne^- \rightarrow M$$

The standard potential of both the anode material Ma and the cathode material Mk must be positive and meet the relation $$\epsilon_{Mk} > \epsilon_{Ma} > 0$$

where $\epsilon_{Mk}$ represents the standard potential of the cathode material Mk, and $\epsilon_{Ma}$ represents the standard potential of the anode material Ma.

The anode material Ma must have a positive standard potential, preferably a standard potential of at least 0.10 V relative to the standard hydrogen electrode (SHE), more preferred at least 0.30 V relative to SHE, yet more preferred at least 0.50 V relative to SHE, and particularly preferred at least 0.75 V relative to SHE. Examples of suitable anode materials are for instance Au and Ag, of which Ag is preferred.

The cathode material Mk must have a standard potential exceeding the potential of an anode material (in the actual case), preferably at least by 0.05 V, more preferred at least by 0.10 V, even more preferred at least by 0.25 V, and most preferred at least by 0.40 V.

Examples of suitable cathode materials combined with Ag as anode material are graphite, Au, Pd, Pt, Ru, Ir ad Rh, of which especially Pd is preferred. When the anode material is Au, it is possible to use Ru, Ir or oxides thereof as cathode material.

Further cathode materials, such as electroactive ceramics which appears electrochemically noble, are also contemplated by the present invention. An example is manganese dioxide which can be manufactured by an electrochermical process, where the material is deposited on the anode at a suitable anodic potential.

Both the anode materials and the cathode material are based on the relevant metals in the metallic form with oxidation step 0, the material according to the invention usually being produced by an application of the cathode material and/or the anode material onto a substrate by way of one or more conventional plating or deposition processes (including electroplating, CVD, PVD, thick film techniques and thermal spraying). However, the anode and/or the cathode material of the active material can be completely or partially converted into a metal compound where the metal has a positive oxidation step, for instance in form of oxide, salt or sulphide.

The conversion into metal with a positive oxidation step can take place during the production of the material as a result of the applied plating processes, by a subsequent treatment or during the application conditions. However, the form of the metal with the positive oxidation step is conditioned by the metal compound in question being sparingly soluble during the application conditions in such a manner that metal ions are not released in toxic amounts to the surrounding electrolyte.

Irrespective of whether it is a question of a metallic form or metal compounds, it is essential to the evaluation of the applicability of the electrode materials that a sufficient difference is ensured between the potentials of the forms in which the metals are present during the application conditions.

Detailed information about electrochemical potentials can be studied using E/pH diagrams based on relevant thermodynamic data from the literature.

The previously suggested antimicrobial materials based on a galvanic effect are designed to provide an iontophoretic effect where the anode material is a metal being converted into antimicrobial metal ions which are released to the surrounding electrolyte. However, the use of anode materials having a positive electrochemical potential implies that the concentration of released metal ions is low and that the cell-inhibiting effect is modest Such a modest effect can be sufficient for an implantate where the effect supports the immune system of the body. However, such a modest effect is not sufficient when used in connection with a preferred embodiment of the present invention, said embodiment dealing with a very efficient control of micro-organisms in connection with for instance food production, treatment of water, such as controlling *Legionella* in public baths and swimming pools, or protecting drinking water in for instance ice cube machines.

The inhibiting material according to the invention has a particular design ensuring a high electric field strength across the entire surface to be provided with a cell-inhibiting effect. In addition, a material having both a good conductivity and catalytic properties is chosen as the anode material.

A sample of the biologically inhibiting material according to the invention has been examined by means of a scanning technique involving a vibrating electrode, viz. a scanning vibrating electrode technique; SVET. The sample is immersed in a 10 mM solution of NaCl at room temperature for up to 24 hours, and local positive and negative currents were measured on the surface. The intensity of these currents remained at the same level during the entire examination which confirms that the biologically inhibiting material presents an electric/catalytic effect.

It turned out surprisingly that such a combination of a structure ensuring high field strengths and the electric and catalytic properties of the anode material provides a cell-inhibiting effect which is significantly stronger than the effect which can be ascribed to released anode metal ions in the liquid acting as an electrolyte.

Without committing ourselves to a specific theory it is assumed that a catalytic oxidation process takes place where small amounts of metal oxide ale converted into metal and oxygen affecting live cells. Thus, when the anode surface comes into contact with a cell which per se represents an oxidizable material and furthermore acts as an electrolyte, said cell is subjected to an oxidation, the reaction at the anode optionally being:

$$2Ma_xO_y \rightarrow 2xMa+yO_2$$

It is assumed that oxygen in statu nascendi is formed at the anode surface when an oxidizable electrolyte, such as a live cell, comes into contact with the anode surface. The cathode has a more positive potential than the anode, and at the cathode the above reaction proceeds in the opposite direction which results in an oxidative regeneration of the surface:

$$2xMa+yO_2 \rightarrow 2Ma_xO_y$$

The particular structure of the inhibiting material according to the invention implies that the electric field strength is sufficiently high everywhere on the cell-inhibiting surface. In addition to the potential difference between the cathode and the anode, the electric field strength is determined by the geometric conditions including the distance between the electrodes.

The structure is characterised by one electrode material being suitably distributed in small isolated areas either in form of microclusters on the surface of the second electrode material or in form of micro-skips in the surface of said second electrode material whereby the neighbouring microclusters or micro-skips are suitably spaced apart without a too long mutual distance.

The distance between these micro-areas should not exceed 400 μm in such a manner that the distance from any point on the active surface both to the adjacent cathode material and to the adjacent anode material does not exceed 200 μm. The distance between the micro-areas is preferably smaller than 150 μm, particularly preferred smaller than 75 μm.

The size of the individual micro-areas should not exceed 50 μm, preferably not 15 μm, particularly preferred not less than 10 μm.

The area ratio of the cathode areas to the anode areas on the active surface is not particularly critical and can for instance be in the range of 0.01:1 to 1:0.01, preferably in the range of 0.05:1 to 1:0.05, such as in the range of 0.15:1 to 1:0.15.

The biologically inhibiting material according to the invention has an inhibiting effect on live cells, including cells of both eucaryotic and procaryotic organisms. By the expression "biologically inhibiting effect" is here meant a reduction or retardation of the cell growth as well as a killing of cells including a disinfection or sterilization.

Thus, the biologically inhibiting material according to the invention can be used within the food industry, such as for sterilizing or retarding the growth of micro-organisms in liquid food products, such as milk products, ice cream, juice, lemonade, gravy, beer and soft drinks, as well as for controlling formation of biofilm on surfaces of products and of equipment at for instance dairies, slaughterhouses, within the fish industry, at the preparation of ready-made dishes, marmalade and jam.

The material according to the invention is furthermore applicable within the pharmaceutical industry for solving hygienic problems.

The material is also useful for limiting the growth of cells in water systems, such as for inhibition of *Legionella* in hot-water pipes, as well as for inhibition of bacterial growth in air-condition systems.

The active surface of the biologically inhibiting material according to the invention results from the second electrode material being applied onto a base of a first electrode material through an incomplete deposition process in such a manner that said second electrode material only partially covers the first electrode material in form of either microclusters or involving micro-skips leaving the first electrode material uncovered.

In principle, the inventive material can be made on the basis of a substrate of the first electrode material, but usually it is based on a substrate of metal, such as for instance stainless steel, polymer or ceramics provided with a coating of the electrode material. Such a coating can be applied by a conventional plating process, such as an electrolytic or autocatalytic, viz. chemical, plating, by way of vapour deposition or depositing through sputtering.

The second electrode material can be applied onto the first electrode material by an electrolytic or chemical deposition through a vapour deposition or depositing by way of sputtering to such a limited extent that the surface of the first electrode material is only partially covered by small clusters or in such a manner that holidays or openings still appear, viz. skips in the layer of the second electrode material.

The biologically inhibiting material according to the invention can also be based on ceramics or polymers, with a large active surface area coated with anode and cathode material, and which in use comes into contact with a thin liquid film in the same manner as in an ion exchanger. Filters or sieves are also possible where the surface of the filter or sieve wires are coated with the biologically inhibiting material. Furthermore, the biologically inhibiting material according to the invention can be in the form of particles coated with anode and cathode material. Such particles can for instance be used as an active filler in coating materials, such as paints.

As stated above the biologically inhibiting material according to the invention can be prepared by means of several per se conventional plating or deposition methods including chemical electrochemical methods, PVD (Physical vapour deposition) CVD (Chemical vapour deposition), thick film techniques and thermal spraying.

Chemical electrochemical methods: The silver coating (anode material) can be applied on electric conducting materials (metals or polymers) by an electroplating process or an electroless process (e.g. autocatalytic), where the anodic materials are deposited as first step followed by the cathodic material which shall be deposited as a non-coherent coating (separately) atop the anode material. The depositions of the cathodic material can be carried out by an ionexchange plating process based on metal ions or metal ion complexes, which has a higher electrochemical potential than the coherent coating (in this case silver). The chemical deposition of the cathodic material is diffusion controlled.

Alternative the process can be carried out in such way, that the cathode surfaces are integrated in the anode as particles or phases. Thus palladium can be dispersed in a coherent silver matrix. Such process can be carried out by alternating treatment of the surface with silver and palladium, deposited by chemical and electrochemical methods, as described above. Especially process techniques based upon coil coating and reel to reel plating can be usable techniques.

Alternating deposition in a one step process based on pulse plating techniques is a further possibility. Another method for integrating the cathode material in the anode material as described above is dispersion plating, where the particles of the cathode material is co-deposited in a matrix continuously under the electrolytic or the electroless deposition process.

PVD (Physical vapour deposition): Techniques such as PVD, where periodical sputtering of cathode and anode materials or electron-beam evaporation from at least two sources of materials (cathode and anode materials) is also considered as an attractive method for manufacturing of the coatings. Especially for coatings on ceramics and polymers with "short lifetime" for application (thickness in the range of 100 nm). This technique can be particular suitable for disposable goods.

CVD (Chemical vapour deposition): Process methods based on decomposition of metal containing gases, which decompose on the surface by thermal and/or plasma activation. Thus gases containing volatile Ag and a noble material may be deposited together or the one after the other.

Thick film techniques: Anodic and chatodic material are applied to the surface by a spray or paint process and later "cured" or sintered by heat treating. The methods also includes processes where thermal decomposition of metal compounds such as $Ag_2O$ or $[Pt(NH_3)_4]Cl_2$ is carried out.

Thermal Spraying of a suitable mix of cathode and anode material to the surface. Thermal spraying covers several processes such as plasma spraying, arc spraying, flame spraying etc.

The growth inhibitive effect of the biologically inhibiting material according to the invention has been demonstrated against *Shewanella putrefaciens* (fish putrefactive bacteria), *Escherichia coli* and *Bacillus cereus*.

BRIEF DESCRIPTION OF THE DRAWINGS

FIG. 1 illustrates a wall of stainless steel 2 in an apparatus, such as for instance an apparatus for processing a dairy product, such as a pasteurizing apparatus, and this wall is on the inner side coated with a continuous layer of an anode material 4 of for instance silver. A plurality of clusters 6 of cathode material, such as palladium, is applied onto the anode material 4. When the inner side is in contact with an electrolyte 8, a potential difference Δp is generated between the potential $p_A$ of the anode material 4 and the potential $p_K$ of the cathode material 6. A bacteria 10 coming close to the inhibiting material is subjected to a high electric field strength $E=\Delta p_B/L_B$, where $\Delta p_B$ is the potential difference across the length $L_B$ of the bacteria. When it is assumed that the presence of the bacteria does not change the field lines significantly, cf. the dotted lines, the path $L_B$ of the field line through the bacteria is of a considerable size, i.e. the ratio $L_B/L_T$ is relatively high where $L_T$ corresponds to the total length of the field line in question, cf. FIG. 1A. A uniform field strength along each field line has the effect that the bacteria is subjected to a potential difference $\Delta p_B=\Delta p\times(L_B/L_T)$, i.e. a relatively high potential when the ratio $L_B/L_T$ is high.

FIG. 2 shows for comparison a schematic view of the principle described in U.S. Pat. No. 4,886,505 (Haynes et al.), where an article 102 is coated on one half of the surface with an anode material 104 and on the other half of the surface with a cathode material 106. The function of this principle is conditioned by an electric contact 116 between the anode material 104 and the cathode material 106 at their interface area 112. A bacteria 110 in the interface area 112 between the anode material 104 and the cathode material 106 is subjected to a high potential difference $\Delta p_B$ similar to the potential difference associated with the inhibiting material according to the invention, the ratio $L_B/L_T$ being high here as well. Compared thereto, a bacteria 114 positioned a distance from the interface area 112 is subjected to a significantly weaker potential difference $\Delta p_B$ as the ratio $L_B/L_T$ is significantly lower.

Like in FIG. 1, FIG. 3 illustrates a wall of stainless steel 202 in an apparatus coated on the inner side with a continuous layer of an anode material 204 of for instance silver. An incomplete coating of cathode material 206 of for instance palladium is applied onto the anode material 204. This incomplete coating leaves openings, viz. skips 212, where the anode material 204 is uncovered. A contact between the inner side and an electrolyte 208 generates a potential difference Δp between the potential $p_A$ of the anode material 204 and the potential $p_K$ of the cathode material 206. A bacteria 210 adjacent the inhibiting material is subjected to a strong electric field strength in the same manner as explained in connection with FIG. 1.

Figure 1:
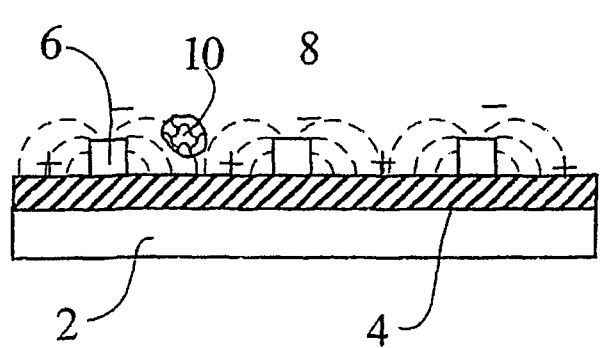
FIG. 1 is a schematic view of an embodiment of the biologically inhibiting material according to the invention.
Figure 1A:
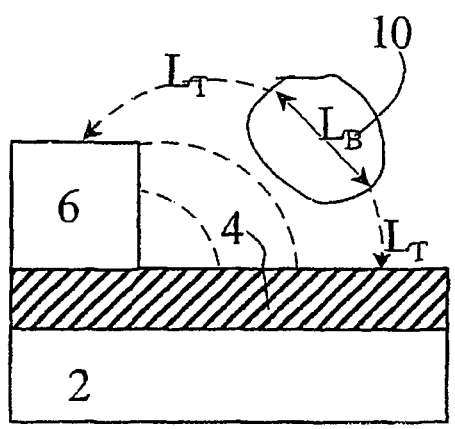
FIG. 1A shows an enlarged detail of FIG. 1.
Figure 2:
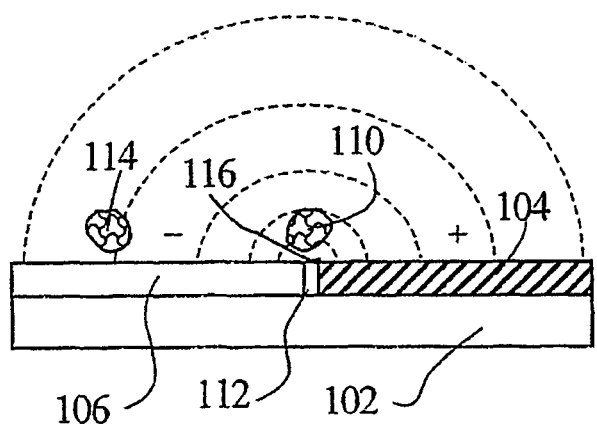
FIG. 2 is a comparing schematic view of the principle described in U.S. Pat. No. 4,886,505.
Figure 3:
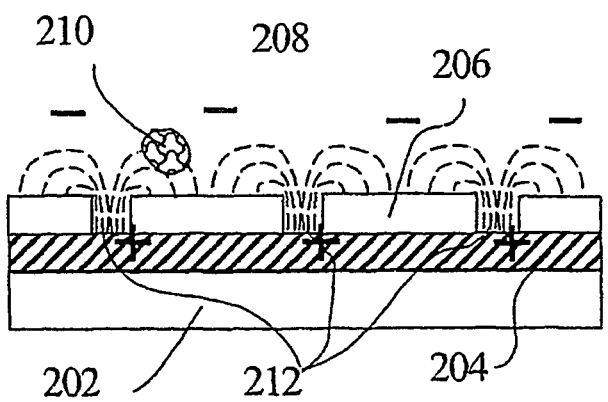
FIG. 3 is a schematic view of an alternative embodiment of the biologically inhibiting material according to the invention.

In a further alternative embodiment the inventive material may have the same design as shown in FIG. 1 but with the cathode material as the continuous layer 4 and the anode material spread as clusters 6 on the surface of the cathode material. In the same way a further embodiment may have the same design as shown in FIG. 3 but with the cathode material as the continuous layer 204 covered with an incomplete coating 206 of anode material.

EXAMPLE 1

Pretreatment

A plate of technical silver (99.75%) of 20×10×1 mm is degreased at room temperature (20 to 25° C.) through an electrolytic degreasing (cathodic) at 10 A/dm² for ten minutes and then rinsed in distilled water. Possible oxides and alkali residues are removed through pickling with dry acid and mechanical agitation for one minute followed by rinsing with distilled water, said dry acid being a solid commercial product based on sodium bifluoride.

Silver Plating

The pre-treated plate is strike silver plated (i.e. is given a short initial silver plating) in a bath containing 3.75 g/l of AgCN (80.5%) and 115 g/l of KCN with stainless steel electrodes at 1 A/dm² for approximately 60 seconds with mechanical agitation. After rinsing in distilled water, a technical silver plating is applied in a bath containing 45 g/l of AgCN (80.5%), 115 g/l of KCN and 15 g/l of $K_2CO_3$ at 1 A/dm² for 20 minutes with mechanical agitation. The plate is rinsed in distilled water and dried in hot air. The thickness of the resulting silver layer is approximately 15 μm.

Stock Solution of Palladium Chloride

A Pd-stock solution of 0.5 g of palladium chloride and 4.0 g of NaCl per 1 of aqueous solution is produced. The solution is shaken and the solution is left over night so as to completely dissolve the solution containing Pd as $Na_2[PdCl_4]$.

Application of Incomplete Pd-Layer

The silver-plating is followed by a degreasing of the plate through an electrolytic cathodic degreasing in cyanide for 20 to 30 seconds, a rinsing, a pickling for 20 to 30 seconds with mechanical agitation and yet another rinsing.

Then the plate is processed by being immersed for 3 minutes in an aqueous solution containing 33% by volume of Pd-stock solution with mechanical agitation. The plate is rinsed in distilled water and dried in hot air. Such a processing results in a reduction of the $PdCl_4^{--}$-ions into metallic palladium according to the reaction:

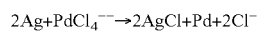

$$2Ag+PdCl_4^{--} \rightarrow 2AgCl+Pd+2Cl^-$$

EXAMPLE 2

A stainless steel plate of 20×10×1 mm of AISI 316 steel with 2 B finish is pre-treated in a conventional manner with Wood nickel strike (100 g/l $NiCl_2$ and 100 ml/l HCl 37%) and strike silver plated in a bath containing 3.75 g/l of AgCN (80.5%) and 115 g/l of KCN with stainless steel electrodes at 1 A/dm² for approximately 60 seconds with mechanical agitation. After rinsing in distilled water, a technical silver plating is applied in a bath containing 45 g/l of AgCN (80.5%), 115 g/l of KCN and 15 g/l of $K_2CO_3$ at 1 A/dm² for 20 minutes with mechanical agitation. The plate is rinsed in distilled water and dried in hot air. The resulting layer of silver has a thickness of approximately 15 μm.

The silver-plating is followed by a degreasing of the surface through an electrolytic cathodic degreasing in cyanide for 20 to 30 seconds, a rinsing, a pickling for 20 to 30 seconds with mechanical agitation and yet another rinsing. Then the plate is immersed for 3 minutes in an aqueous solution containing 33% by volume of the Pd-stock solution of Example 1 with mechanical agitation. The plate is rinsed in distilled water and dried in hot air.

SEM/EDS-analysis (Scanning Electron Microscopy/Energy Dispersive X-ray Spectrometry) of the surface processed in this manner reveals that 15 to 25% of the surface area is covered by silver/silver chloride while the remaining surface area is covered by a thin layer of palladium of approximately 0.1 μm. The areas covered by silver/silver chloride present an extent of from 0.1 μm to 6 μm, and the distance between the individual areas of silver/silver chloride varies from 0.4 μm to 3 μm.

EXAMPLE 3

Method

Untreated stainless steel plates of 20×10×1 mm (control) were placed in one vessel, and silver plates coated with silver and palladium produced according to the invention as described in Example 1 were placed in a second vessel. Equal amounts of milk were added to the two vessels. The temperature was kept at 21° C., and the milk was circulated across the surfaces of the plates. *Escherchia coli* K12 was added to a cell level of the magnitude $10^4$/ml. Sample plates were removed immediately upon the addition of *Escherichia coli* and subsequently every hour for the first 6 hours as well as 24 hours after the start of the experiment. The formation of biofilm on the plates was examined with dyeing and confocal microscopy for protein and fat and with dyeing for live and dead bacteria.

Results

Confocal microscopy clearly demonstrated the presence of biofilm on the control plates where both proteins, fat and bacteria were detected on the surface. However, neither protein, fat nor bacteria were detectable on the plates according to the invention and thus no biofilm was recognizable on the plates according to the invention.

A cell-counting on liquid samples from the two vessels appears from the following table:

TABLE

| | Number of cells/ml | |
|---|---|---|
| Time (hours) after start | Vessel with untreated stainless steel plates (control) | Vessel with silver and palladium coated plates (acc. to the invention) |
| 0 | $32 \times 10^4$ | $33 \times 10^4$ |
| 1 | $29 \times 10^4$ | $34 \times 10^4$ |
| 2 | $36 \times 10^4$ | $26 \times 10^4$ |
| 3 | $34 \times 10^4$ | $27 \times 10^4$ |
| 4 | $49 \times 10^4$ | $39 \times 10^4$ |
| 5 | $69 \times 10^4$ | $56 \times 10^4$ |
| 6 | $73 \times 10^4$ | $71 \times 10^4$ |
| 24 | $10 \times 10^8$ | $79 \times 10^4$ |

It appears from the table that no bacterial growth was detected during the first six hours. After 24 hours, a clear bacterial growth was detected in the control vessel whereas no bacterial growth was detectable in the vessel with the plates according to the invention.

EXAMPLE 4

An incomplete Pd-layer is applied onto a silver plated stainless steel plate of 20×10×1 mm produced as described in Examples 1 and 2 in the same manner as described in Example 1, but with a solution containing 5% of Pd-stock solution and involving a processing time of 1 minute.

EXAMPLE 5

An incomplete Pd-layer is applied onto a silver plated stainless steel plate of 20×10×1 mm produced as described in Examples 1 and 2 in the same manner as described in Example 1, but with a solution containing 5% of Pd-stock solution and involving a processing time of 3 minutes.

EXAMPLE 6

An incomplete Pd-layer is applied onto a silver plated stainless steel plate of 20×10×1 mm produced as described in Examples 1 and 2 in the same manner as described in Example 1, but with a solution containing 33% of Pd-stock solution and involving a processing time of 1 minute.

The plates produced according to the Examples 3 to 6 were examined by an SEM/EDS-analysis This analysis revealed that an increased concentration of Pd-stock solution as well as a prolonged processing time result in an increased application of Pd. However, all plates still showed surface areas with silver/silver chloride alternating with areas of Pd, and a bacterial inhibiting effect was detected on all the plates.

EXAMPLE 7

A layer of silver and palladium is applied onto spiral wires of technical silver (99.75%) of a thickness of 0.5 mm in the same manner as described in Example 1. The spiral wires are suited for biological inhibition through immersion in biologically sensitive liquids.

EXAMPLE 8

A spiral wire produced according to Example 7 with an active surface of 160 $cm^2$ was immersed in a 3 l cleaned watering arrangement placed outdoors in a poultry keeping of 8 hens of the breed Buff Orpington. The reservoir of the watering arrangement was filled with 2 l of tap water. The water in the water reservoir kept fresh for several days, and no formation of biological slime was observed on the plastic surfaces apart from the external drinking bowl, where the water had left the reservoir with the spiral wire. However, the formation of slime in the drinking bowl was reduced compared to the usual formation of slime. After 3 days and nights, approximately 0.5 l of water was left, and this water was collected together with the dirt and gravel scraped into the drinking bowl by the hens. After filtration, both the filtrate and the solid gravel fraction were examined with respect to content of silver by way of atomic absorption (AAS). Both fractions disclosed a silver content significantly lower than 100 μg/l.

The above description of the invention reveals that it is obvious that it can be varied in many ways. Such variations are not to be considered a deviation from the scope of the invention and all such modifications which are obvious to persons skilled in the art are also to be considered comprised by the scope of the succeeding claims.

The invention claimed is:

1. A method for inhibiting live cells including eukaryotic and prokaryotic cells on an item having a biologically inhibiting material, the method comprising:
providing food, liquid food product or drinking water; and
contacting the food, liquid food product or drinking water with the biologically inhibiting material that comprises
an anode material which does not dissolve during a galvanic process such that a silver ion content released is less than 100 µg/l, and
a cathode material,
wherein both of the anode material and the cathode material have a positive galvanic potential,
wherein the potential of the cathode material is higher than the potential of the anode material,
wherein the anode material and the cathode material each comprise exposed active surfaces with separated areas of anode material and cathode material, and
wherein a distance between any point on the active surface and both the adjacent cathode material and the adjacent anode material does not exceed 200 µm for inhibiting live cells by oxidation on the surface of the biologically inhibiting material.

2. The method according to claim 1, wherein the distance from any point on the surface both to the adjacent cathode material and to the adjacent anode material does not exceed 100 µm.

3. The method according to claim 1, wherein an area ratio in a plane of the surface of the areas of cathode material to the areas of anode material is in the range of 0.01:1 to 1:0.01.

4. The method according to claim 3, wherein the area ratio in the plane of the surface of the areas of cathode material to the areas of anode material is in the range of 0.05:1 to 1:0.05.

5. The method according to claim 1, wherein on the surface of the biologically inhibiting material, the cathode material and the anode material are placed in separate areas relative to one another and distributed across a continuous area of a second electrode material.

6. The method according to claim 5, wherein the largest dimension of the individual separated areas in the plane of the surface is smaller than 15 µm.

7. The method to claim 5, wherein the distance between adjacent separated areas in the plane of the surface is less than 10 µm.

8. The method according to claim 1, wherein the anode material is Au or Ag.

9. The method according to claim 8, wherein the anode material is Ag, and that the cathode material is a material selected from the group consisting of graphite, Au, Pd, Pt, Ru, Ir and Rh.

10. The method according to claim 1, wherein the item utilized outside of the human body comprises equipment for at least one of food preparation and drinking water systems.

11. The method according to claim 2, wherein on the surface of the biologically inhibiting material the cathode material and the anode material are placed in separate areas relative to one another and distributed across a continuous area of a second electrode material.

12. The method according to claim 3, wherein on the surface of the biologically inhibiting material the cathode material and the anode material are placed in separate areas relative to one another and distributed across a continuous area of a second electrode material.

13. The method according to claim 4, wherein on the surface of the biologically inhibiting material the cathode material and the anode material are placed in separate areas relative to one another and distributed across a continuous area of a second electrode material.

14. The method according to claim 6, wherein the distance between adjacent separated areas in the place of the surface is less than 10 µm.

15. The method according to claim 2, wherein the anode material is Au or Ag.

16. The method according to claim 3, wherein the anode material is Au or Ag.

17. The method according to claim 2, wherein the biologically inhibiting material is a constructional material in equipment for food preparations or in drinking water systems.

18. The method according to claim 3, wherein the is a constructional material in equipment for food preparations or in drinking water systems.

19. A method for inhibiting live cells, comprising:
providing food, liquid food product or drinking water; and
contacting the food, liquid food product or drinking water with a biologically inhibiting material which comprises
an anode material having a positive galvanic potential which does not dissolve during a galvanic process such that a silver ion content released is less than 100 µg/l, and
a cathode material provided in small isolated areas on a surface of the anode material, the cathode material having a positive galvanic potential higher than the galvanic potential of the anode material.

* * * * *